United States Patent [19]
Yamasaki

[11] Patent Number: 5,279,781
[45] Date of Patent: Jan. 18, 1994

[54] MELT-SPIN PROCESS FOR ELECTROCONDUCTIVE FIBERS USED IN HUMAN-IMPLANTABLE ELECTRODE AND CLOTH

[75] Inventor: Haruki Yamasaki, Isehara, Japan

[73] Assignee: Tanaka Kikinzoku Kogyo K.K., Japan

[21] Appl. No.: 700,596

[22] Filed: May 15, 1991

[30] Foreign Application Priority Data

Jun. 12, 1990 [JP] Japan .................. 2-153466
Jun. 12, 1990 [JP] Japan .................. 2-153467
Aug. 31, 1990 [JP] Japan .................. 2-229593

[51] Int. Cl.$^5$ .......................... C04B 35/00
[52] U.S. Cl. .................... 264/104; 264/171; 264/210.8; 264/290.5; 425/133.1
[58] Field of Search ........... 427/244, 407.1, 434.6, 427/125; 428/379, 395, 365; 57/257, 258, 245, 310, 400; 623/74, 900, 901; 264/104, 171, 210.8, 200.5; 425/133.1

[56] References Cited

U.S. PATENT DOCUMENTS

| | | | |
|---|---|---|---|
| 3,958,066 | 5/1976 | Imamura et al. | 428/395 |
| 4,042,737 | 8/1977 | Forsgren et al. | 427/125 |
| 4,547,420 | 10/1985 | Krueger et al. | 264/171 |
| 4,663,221 | 5/1987 | Makimura et al. | 264/171 |
| 4,721,551 | 1/1988 | Byers et al. | 623/24 |
| 4,743,505 | 5/1988 | Yamada et al. | 428/379 |
| 5,030,077 | 7/1991 | Orimoto et al. | 425/133.1 |

*Primary Examiner*—Shrive Beck
*Assistant Examiner*—Benjamin Z. Utech
*Attorney, Agent, or Firm*—Klauber & Jackson

[57] ABSTRACT

Electroconductive fibers are made by melt-spin coating of chemical fibers with Pt, Ti, Ta or alloys containing of Pt, or Ti. The coated fibers are utilized in human-implantable electroconductive cloth electrodes with improved metal fatigue resistance and/or electrode uniformity.

1 Claim, 1 Drawing Sheet

MELT-SPIN PROCESS FOR ELECTROCONDUCTIVE FIBERS USED IN HUMAN-IMPLANTABLE ELECTRODE AND CLOTH

BACKGROUND OF THE INVENTION

The present invention relates to an electrode employed in the field of medical equipment, more in detail to an implantable mesh electrode, especially an electrode for reanimation, and to a process for preparing electroconductive fibers and cloth suited for preparing same.

Heretofore, a mesh electrode has been employed which is formed by fine fiber of Pt-Ir (10%) of Ti in the viewpoint of its electric characteristics and its suitability to human organs in the field of medical equipment or the like. For example, the electrode for reanimation of a patient of cardiac paralysis which is formed by weaving fine fibers of Pt-Ir(10%) or Ti having an outer diameter of about 0.1 mm into a mesh in the form of a heart by means of laser cutting or the like is stuck to the outer wall of a cardiac muscle. In case of emergency of cardiac paralysis or the like, a large current of several amperes is flown in the electrode to bring the troubled cardiac muscle to life.

However, the mesh of Pt-Ir(10%) of Ti lacks flexibility and locally makes a space between the mesh and a heart wall. The heat is sometimes generated on the locally contacted portions to make a burn thereon to injure the tissues of the cardiac muscle.

Due to the metal fatigue generated by the repeated stress of the beating of the heart, a crack is sometimes formed in the fine fibers because the mesh of Pt-Ir(10%) or Ti is made of metal.

In the meantime, implantable electroconductive cloth for the electroconductive cloth electrodes has been known which is formed by electroless-plating Pt on polyester cloth, or by plating or vapor-depositing Pt, Ti or Ta on synthetic fibers.

The former electroconductive cloth possesses a drawback that plating residue of the electroless plating may remain in the apertures of the cloth. The latter electroconductive cloth possesses a drawback that the coating may be non-uniformly deposited since it is made by plating or vapor-depositing the metal on the synthetic fibers. Therefore, the electroconductivity of the both electrodes is uneven.

SUMMARY OF THE INVENTION

The present invention has been made to overcome the above problems.

An object of the present invention is to provide an implantable electroconductive cloth electrode possessing sufficient flexibility.

Another object of the invention is to provide an implantable electroconductive cloth electrode injuring no or little cardiac tissues and generating no fatigue failure.

A further object of the invention is a process for preparing implantable electroconductive fibers or cloth excellent in electroconductivity which is especially suited for preparing the above electrode.

The technical means of the present invention to overcome the above problems is an implantable electroconductive cloth electrode characterized in that the cloth is formed by chemical fibers the surface of which is coated with Pt, Ti or an alloy containing Pt and/or Ti.

Another aspect of the present invention is a process for preparing implantable electroconductive fibers excellent in electroconductivity having chemical fibers filled with a filler Pt, or Ti, and Ta or an alloy on its outer surface and containing no residue, and for preparing implantable electroconductive cloth of which coating is uniformly deposited and of which electroconductivity is even.

A process for preparing implantable electroconductive fibers for overcoming the above problems comprises introducing a liquid containing mixed melt of synthetic resin chip and staple filler selected from the group consisting of Pt, Ti and an alloy of Pt, Ti, and Ta into a liquid supply port of an outer side of a composite metal base for spinning, introducing melted synthetic resin into a liquid introduction port of an inner side, discharging the liquid and the melted resin through discharging ports at the end of metal base connected to the respective introduction ports, stretching and spinning them to prepare electroconductive fibers made of synthetic resin around which is formed the filler.

A process for preparing implantable electroconductive cloth comprises weaving the fiber prepared as described above to form electroconductive cloth and coating the electroconductive cloth with silicon resin.

DETAILED DESCRIPTION OF THE INVENTION

Figure 1:
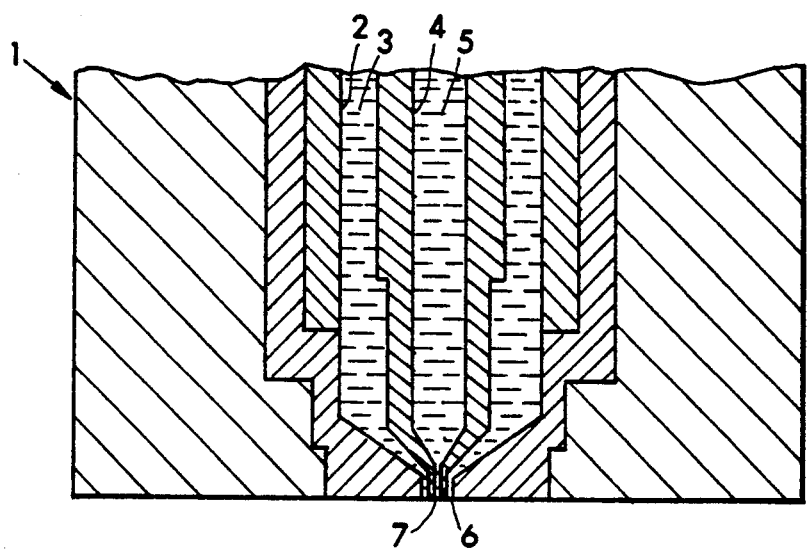

In the course of the manufacture of the cloth, Pt, Ti an alloy containing Pt and/or Ti may be coated on the chemical fibers which are then woven, or may be coated on the woven cloth.

According to the implantable electroconductive cloth electrode of this invention, the electrode comprising cloth made of chemical fibers coated with Pt, Ti or its alloy and possessing high flexibility can be uniformly stuck to an outer wall of a heart to follow the beating of the heart so that the implantable electroconductive cloth electrode of this invention creates no inconveniences such as peeling and formation of a space, uniformly supplies a current to a cardiac muscle not to injure tissues and possesses the excellent electrode characteristics producing little fatigue failure.

The mesh of the implantable electrode of this invention may be filled with silicon resin to depress excessive growth of human organ tissues and to prevent peeling of the metal coating.

According to the above implantable electroconductive cloth electrode of the invention, since the electrode which is formed by the cloth of chemical fibers possesses excellent flexibility and stretchability, and is uniformly stuck to the outer wall of a cardiac muscle to follow the beating of a heart, no inconveniences such as peeling and formation of a space are generated. Further, when a large current is flown in case of emergency, a burn is not formed to injure the tissues because the current is uniformly supplied to the cardiac muscle. No or little fatigue failure is produced because the raw material is chemical fibers. Since, further, the surface of the fibers is coated with Pt, Ir or its alloy having excellent electric characteristics, compatibility to human organs and corrosion resistivity and no toxicity, an implantable electrode having excellent characteristics can be obtained.

Although as chemical fibers polyester resin having flexibility and stretchability is appropriate, other resin such as nylon, acryl resin, polypropylene resin may be employed. While such a dry plating technique as vapor deposition and sputtering and such a wet plating technique as electroless plating are employed for coating, the electroless plating is superior from the viewpoint of penetration into the fibers.

Although the coating thickness of not less than 1 mm may be required to produce the remarkable effectiveness, the thickness may be determined at discretion. By employing the cloth of chemical fibers coated with the metals in this invention, the electroconductivity at the contacted portions can be secured.

The mesh of the implantable electrode of this invention may be filled with silicon resin to depress excessive growth of human organ tissues and to prevent peeling of the metal coating.

Since, in the process for preparing implantable electroconductive fibers of this invention, the fibers are stretched and spun by discharging the melted synthetic resin containing the filler selected from the group consisting of Pt, or Ti, Ta and or an alloy containing any or all of Pt, Ti and the usual melted resin through the discharging ports disposed concentrically employing the composite metal base for spinning, no impurities nor poisonous substances are produced. Since the synthetic resin containing the filler is uniformly disposed on the outer surface, uniform and excellent electroconducitivty can be obtained.

Since, in the process for preparing the implantable electroconductive cloth of this invention, the electroconductive cloth is formed by weaving the above fibers and coating the electroconductive cloth with the silicon resin, the coating is uniformly formed to provide the excellent electroconductivity. Accordingly, the cloth can be suitably employed for preparing a reamination electrode for a patient of cardiac paralysis, or for such an implantable electrode as an electrode for promoting bone growth.

According to the process for preparing the implantable electroconductive fibers, the implantable electroconductive fibers can be obtained which possess uniform and excellent electroconductivity because the chemical fibers containing the Pt, or Ti, Ta or an alloy of Pt, Ti, filler are uniformly disposed on the outer surface thereof.

Further, according to the process for preparing the implantable electroconductive cloth, the implantable electroconductive cloth can be obtained which is suitably employed for preparing a reamination electrode for a patient of cardiac paralysis, or such an implantable electrode as an electrode for promoting bone growth because the coating of the silicon is uniformly deposited to supply the excellent electroconductivity.

DETAILED DESCRIPTION OF THE DRAWINGS

Figure 2:

FIG. 1 shows one example of an apparatus employed for implantable electroconductive fibers in this invention, FIG. 2 is a sectional view of the implantable electroconductive fiber obtained thereby.

EXAMPLES

Examples of the present invention will be described together with Comparative Examples.

EXAMPLE 1

Surface coating of 4 $\mu$m of Pt was formed around fiber made of polyester having a fiber diameter of 10 $\mu$m by means of electroless plating. The lints were then woven to electroconductive cloth of 100 mm $\times$ 100 mm. After the mesh was filled with silicon resin and dried to be solidified, it was cut into a circular element having an outer diameter of 50 mm to which a lead was connected to prepare an implantable electroconductive cloth electrode.

COMPARATIVE EXAMPLE 1

A circular implantable electrode of 50 mesh having an outer diameter of 50 mm was prepared with metal fibers of Pt-Ir(10%) having a fiber diameter of 100 $\mu$m.

A current of 2 A was flown for 30 minutes at 10 V in an electrolyte consisting of 9 g of NaCl, 1000 g of $H_2O$ and 1000 g of an alcohol employing the above cloth electrode as a cathode and a plate electrode of Ti having the dimensions of 30 mm $\times$ 40 mm as an anode. The number of times of bendings required to produce a crack in the fibers of the electrodes before and after the electrolysis when the electrode was rectangularly bent and its specific resistance were as shown in the below Table.

EXAMPLE 2

After polyester fiber having a fiber diameter of 10 $\mu$m were woven to polyester cloth of 100 mm $\times$ 100 mm, surface coating of 4 $\mu$m of Pt was formed around the cloth by means of electroless plating. After the mesh was filled with silicon resin and the cloth was dried for solidification, it was cut into a circular element having an outer diameter of 50 mm to which a lead was connected to prepare an implantable electroconductive cloth electrode.

COMPARATIVE EXAMPLE 2

A circular implantable electrode of 50 mesh having an outer diameter of 50 mm was prepared with metal fibers of Pt-Ir(10%) having a fiber diameter of 100 $\mu$m.

The number of times of bendings and the specific resistance of the electrodes of Example 2 and of Comparative Example 2 were measured under the same conditions of Example 1 and Comparative Example 2.

TABLE

| | Number of Times of Bending | | Specific Resistance ($\mu\Omega$cm) |
|---|---|---|---|
| | Before Electrolysis Test | After Electrolysis Test | |
| Example—1—; | $5 \times 10^6$ | $5 \times 10^6$ | 53 |
| Comp. Ex—1—; | $5 \times 10^5$ | $5 \times 10^5$ | 55 |
| Example—1—; | $5 \times 10^6$ | $4 \times 10^6$ | 55 |
| Comp. Ex—1—; | $5 \times 10^5$ | $5 \times 10^5$ | 55 |

As apparent from the foregoing, the implantable electroconductive electrodes of these Examples possess excellent fatigue characteristic superior to that of the electrodes of Comparative Examples and possess excellent specific resistance the electrodes of Comparative.

Also in the implantable electroconductive cloth electrode coated with Ti in place of Pt, excellent fatigue characteristic and specific resistance were obtained.

Further coating of the metals on the surface of the cloth electrode results in better performance.

EXAMPLE 3

This Example is to exemplify the preparation of implantable electroconductive fibers.

As shown in FIG. 1, a mixed and melted liquid 3 containing polyester chip and a electroconductive staple filler of Pt having a diameter of 0.5 μm and a length of 0.5 to 2 mm was introduced into a liquid introduction path 2 of a composite base 1 for spinning consisting of an inner side and an outer side, while melted polyester 5 was introduced into an introduction path 4 of the inner side. The liquid 3 and the melted polyester 5 were discharged respectively through the discharging ports 6,7 at the end of the base 1 connected to the respective introduction paths 2,4, stretched and spun to obtain an electroconductive fiber 8 made of polyester containing the Pt filler on its outer surface as shown in FIG. 2.

Since the polyester containing the Pt filler was uniformly disposed on the outer surface of the electroconductive fiber 8 thus obtained, the fiber 8 possessed uniform and excellent electroconductivity.

Then, the electroconductive fiber 8 was woven to make electroconductive cloth on which was coated silicon resin to prepare implantable electroconductive cloth.

The coating of the silicon resin of the implantable electroconductive cloth thus obtained is uniformly deposited so that the cloth possesses excellent electroconductivity. Accordingly, the cloth can be employed for preparing a reamination electrode for a patient of cardiac paralysis, or such an implantable electrode as an electrode for promoting bone growth having stability of operation and reliability.

Although in this Example the electroconductive fiber of polyester containing the Pt filler on the outer surface, the invention is not restricted thereto. The Pt filler may be replaced with a or Ti or Ta filler, or an alloy filler. The fiber substrate is not restricted to the polyester, and acryl resin or polypropylene may be employed.

What is claimed is:

1. A process for preparing an implantable electroconductive fiber which comprises the steps of introducing a liquid containing a mixed melt of synthetic resin and a filler material selected from the group consisting of Pt, Ti, Ta and alloys containing any of Pt and Ti; into a first liquid supply port of a composite metal base for spinning; said metal base having a hollow inner core and an outer hollow section, concentric around the inner core, with said liquid being introduced into the outer hollow section via the first liquid supply port; introducing melted synthetic resin into a second liquid introduction port to the hollow inner core; discharging the liquid and the melted resin from respective adjacent discharging ports of metal base arranged whereby the melted synthetic resin is surrounded by the liquid with said discharging; and stretching and spinning the discharged melted synthetic resin and mixed melt to prepare an electroconductive fiber made of synthetic resin around which is formed the filler material.

* * * * *